United States Patent [19]

Bloomster et al.

[11] Patent Number: 4,873,126

[45] Date of Patent: Oct. 10, 1989

[54] SYSTEM AND PROCESS FOR SPOTTING REAGENTS ON POROUS SUPPORTS

[75] Inventors: Timothy G. Bloomster, Shrewsbury, Pa.; Hans H. Feindt, Parkton, Md.; Gerald D. Hahn, Lothian, Md.; S. Melissa Maret, Damascus, Md.

[73] Assignee: Becton, Dickinson and Company, Franklin Lakes, N.J.

[21] Appl. No.: 232,209

[22] Filed: Aug. 15, 1988

[51] Int. Cl.$^4$ .......................... B05D 3/00; B05C 3/18; B05C 3/20

[52] U.S. Cl. .................................... 427/282; 118/50; 118/406; 118/415; 427/2; 427/296

[58] Field of Search .................. 427/2, 258, 282, 243, 427/296; 118/406, 415, 401, 50

[56] References Cited

U.S. PATENT DOCUMENTS 3,876,449  4/1975  Smith et al. ........................ 427/282
4,748,042  5/1988  Limmecke et al. ..................... 427/2

*Primary Examiner*—Evan Lawrence
*Attorney, Agent, or Firm*—Mary M. Allen

[57] ABSTRACT

A system having a coating station comprised of a dispensing assembly and a fluid collection head is useful in a method to precisely coat reagents on porous supports for use in diagnostic devices. In the method, a cover having an aperture therethrough and the porous support secured to its underside covering the aperture is positioned in the coating station between the dispensing assembly and the fluid collection head. The reagent is dispensed from a cannula in the dispensing assembly onto the portion of the porous support exposed through the aperture of the cover. A reduced pressure in the fluid collection head pulls fluid through the porous support. The system is automated by providing a guide channel for holding a plurality of covers in correct orientation and a magazine for holding a stack of covers. An indexing arm delivers the bottom-most cover in the stack to the guide channel and urges covers in the channel along its length. The system includes a reciprocating cylinder to bring the dispensing assembly and fluid collection head to the cover for coating and away from the cover after coating. The dispensing assembly may include a template for coating the reagent in a distinct pattern. The system can include a plurality of coating stations to permit coating with a plurality of reagents.

18 Claims, 2 Drawing Sheets

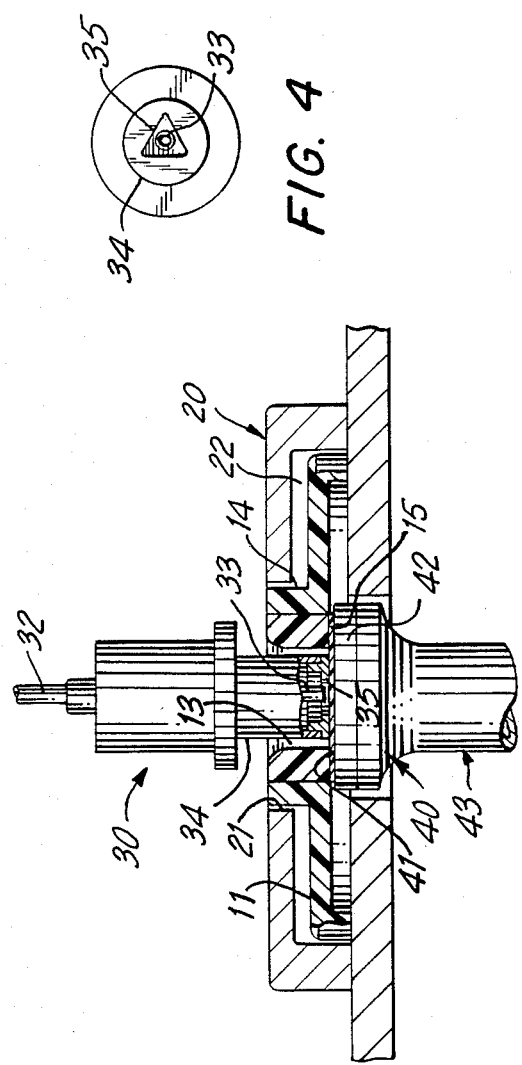
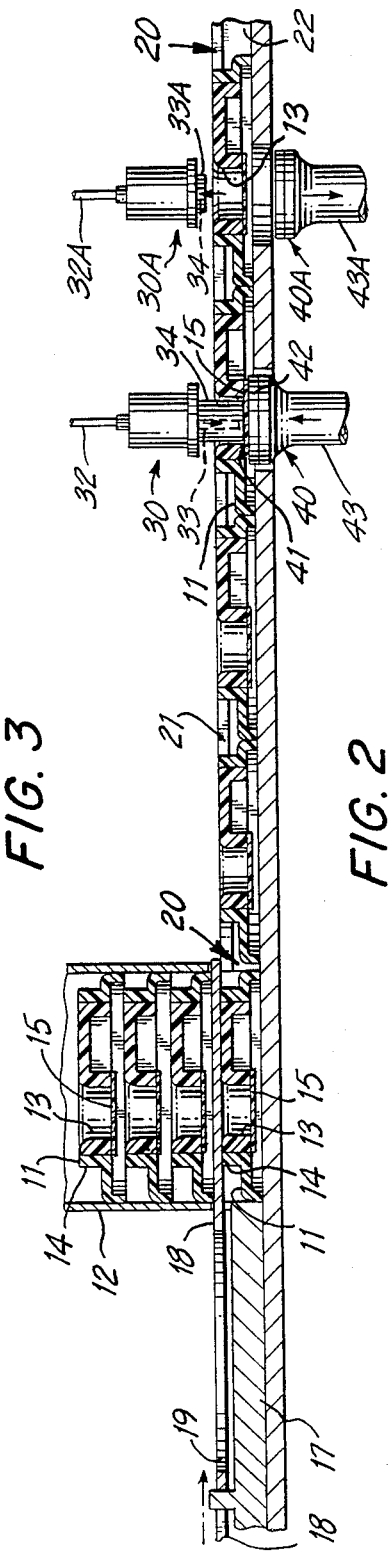

SYSTEM AND PROCESS FOR SPOTTING REAGENTS ON POROUS SUPPORTS

FIELD OF THE INVENTION

The present invention relates to systems and processes to manufacture diagnostic devices having one or more reagents coated on a porous support. More particularly it relates to a system and process for achieving precise placement of one or more reagents on a porous support.

BACKGROUND OF THE INVENTION

Numerous diagnostic devices have recently been introduced for use by relatively unskilled personnel. One such device is described in U.S. Ser. No. 106,757 filed Oct. 8, 1987. The system described is a flow-through device with having a porous support and an absorptive layer. A binder is immobilized on a test area of the porous support.

In use sample and assay reagents are allowed to flow through the porous support to the absorptive layer. The presence or absence of a visible signal on the test area indicates the presence or absence of analyte in the sample. The preferred device shown has a triangular test area surrounded by a background area of the porous support. The background area is desirable so that a visible signal on the test area contrasts from the unreacted background area.

Other devices have been introduced with reagents coated in patterns such as round dots, bars resembling a "minus" sign, and crosses resembling a "plus" sign. Some devices have multiple reagents immobilized on the support. For example some have positive controls, negative controls, or both.

These devices all have in common a support having one or more reagent immobilized at or near a surface. The surface bearing the reagent is then assembled in the device so that a fluid sample and assay reagents are deposited on the coated surface during the assay. Many of these devices also have one or more reagent coated in a distinct pattern. In each case the portion of the support bearing the immobilized reagent has a specific position within the test device. Where the device has multiple reagents immobilized, the reagents are positioned precisely in relation to each other and the device in distinct patterns.

Locating the reagents on the supports in the correct position and shape is difficult to accomplish in a cost effective manner. Manual spotting is time consuming and labor intensive. When the reagents are manually spotted, rejection rates are generally high because of unacceptable variations in spot location, concentration, and shape. The devices need to be equivalent to each other for quality assurance. This is particularly important for devices to detect viral antigens or antibodies to viral antigens such as HIV.

One system to facilitate correct placement of the reagent is described in U.S. Ser. No. 106,075 filed Oct. 8, 1987. In that system the binder is spotted in admixture with a marker so that the location of the binder can be detected when spotting a control reagent and when assembling the support into the device. The preferred device incorporates fluorescent dyes allowing quality control of devices prior to final assembly thereby reducing waste.

Another proposed solution to the problem of coating reagents is described in U.S. Pat. No. 4,748,042. That system uses "means for forming a transferable pattern" to transfer an antibody solution to a protein binding membrane. The particular means described is a foam pad. According to the patent the amount of fluid to be pumped onto the head is determined empirically by observing the quality of the markings on each membrane. When the quality has deteriorated to a predetermined level of poor quality new fluid is injected into the head. The patent recommends incorparating a dye so that an assembly operator can inspect the membranes. See col 3, lines 55–62 and col 4, lines 27–33. This design inherently suffers from concentration variations as the transfer surface is depleted of fluid. Another problem with the design is controlling the pressure with which the transfer surface contacts the membrane. The patent emphasizes the problem of damaging delicate membranes so that they are not useful in diagnostic devices. Nonetheless, the transfer surface must contact the membrane with sufficient force to transfer the antibody solution. As the transfer surface wears and as the volume of fluid on the transfer surface varies, the contact pressure of the transfer surface will be very difficult to control.

Accordingly, a need exists for an inexpensive, automatible system to locate precisely measured amounts of one or more reagents on a support and to locate precisely the immobilized reagent(s) within the assembled device.

SUMMARY OF THE INVENTION

The present invention overcomes the difficulties in coating reagents on supports by providing a reproducible method and system for accurately locating one or more reagents on a porous support. In the method an upper surface of the porous support is secured to a cover which has an aperture. The cover is positioned within a coating station with its aperture between a dispensing assembly and a fluid collection head. The dispensing assembly has a dispensing cannula. The distance between the dispensing assembly and the fluid collection head is decreased until the fluid collection head contacts the lower surface of the porous support and the dispensing cannula is sufficiently close to the upper surface of the porous support that a fluid dispensed through the dispensing cannula will contact the support in the area within the aperture. Where a spot having a specific pattern surrounded by a background area is desired, the dispensing assembly includes a template which engages the upper surface of the support. The reagent is dispensed while a vacuum is applied to the lower surface of the support to reduce the pressure sufficiently to pull the liquid through the support leaving the reagent on the support.

In this manner a uniform coating is deposited on the support. The volume of fluid dispensed can be controlled to assure that the amount of reagent coated is the same from device to device. Where a template is used the coating has clean edges as defined by the template. The location of the reagent is precisely located with respect to the aperture in the cover by virtue of the positioning step. The use of a cover with the support secured to it and the step of decreasing the distance between the dispensing assembly and the fluid collection head assure that a minimal force is applied to the porous support during coating. This is particularly advantageous when the porous support is a delicate membrane. The cover and porous support bearing its reagent(s) can then be assembled into the test device with the cover becoming the cover of the device.

The reagents that can be coated with the present invention include any that would be useful on a porous support of a diagnostic device. Trapping molecules such as antigens and antibodies, positive control solutions, negative control solutions, blocking solutions, and buffers are all usefully coated with the present process. The reagents can be secured on the support by the binding properties of the support or by the binding properties of other reagents previously coated. For example protein antigens and antibodies are bound by protein binding membranes. Where a carbohydrate control antigen is desired, it can be bound to an antibody previously coated on the porous support.

The coating system of the present invention comprises a guide channel for delivering and positioning the cover in a coating station. The coating station is comprised of a fluid collection head positioned to pull fluid through the porous support and a dispensing assembly. The fluid collection head has a vacuum source to provide a pressure sufficiently low to pull a fluid through the porous support. The dispensing assembly has a dispensing cannula and optionally includes a template. The system also has reciprocating means to decrease the distance between the dispensing assembly and the fluid collection head so that a porous support positioned between the dispensing assembly and the fluid collection head is contacted on its lower surface by the fluid collection head and its upper surface is sufficiently close to the dispensing cannula to receive on its upper surface in the area defined by the aperture a reagent dispensed from the dispensing cannula. When a template is included the reciprocating means decreases the distance between the fluid collection head and the dispensing assembly until the upper surface of the support is contacted by the template.

Preferably the reciprocating means comprises two pneumatic cylinders. The first serves to bring the fluid collection head towards the dispensing assembly for coating and to remove the fluid collection head from the porous support after the support has been coated. The second is to bring the dispensing assembly towards the upper surface of the porous support and to remove the dispensing assembly after coating of the reagent.

A plurality of reagents can be coated by combining a plurality of dispensing cannulas within a single coating station or by using a plurality of coating stations. The additional reagents can be coated at a location on the support different from the first or superimposed (partially or entirely over the first reagent. Where the reagents are located remote from each other, they may be coated simultaneously. Where the reagents are to be partially or totally superimposed, the coating steps are conveniently performed sequentially.

The system is readily automated by incorporating indexing means to move a cover from a starting position, to the coating station, to any additional coating stations, and finally to a finish position. Most preferably the system includes indexing means for taking a cover from a stack and delivering it to the guide channel. The preferred indexing means is an indexing arm for sequentially feeding a plurality of covers to the guide channel.

As those skilled in the art will appreciate, the system can also include drying stations to dry coated reagents with forced air, with vacuum, or with lyopholization. The templates can be configured in any patterns desired. Preferably the templates are removably mounted so that they can be interchanged when desired.

BRIEF DESCRIPTION OF THE DRAWINGS

FIG. 2 shows a sectional view of the system taken along section line 2—2 of FIG. 1;

FIG. 3 shows a sectional view of the system taken along section 3—3 of FIG. 1; and FIG. 4 shows a end plan view of the dispensing cylinder, dispensing cannula, and template included in the coating station 30 shown in FIG. 2.

DETAILED DESCRIPTION OF THE INVENTION

Figure 1:
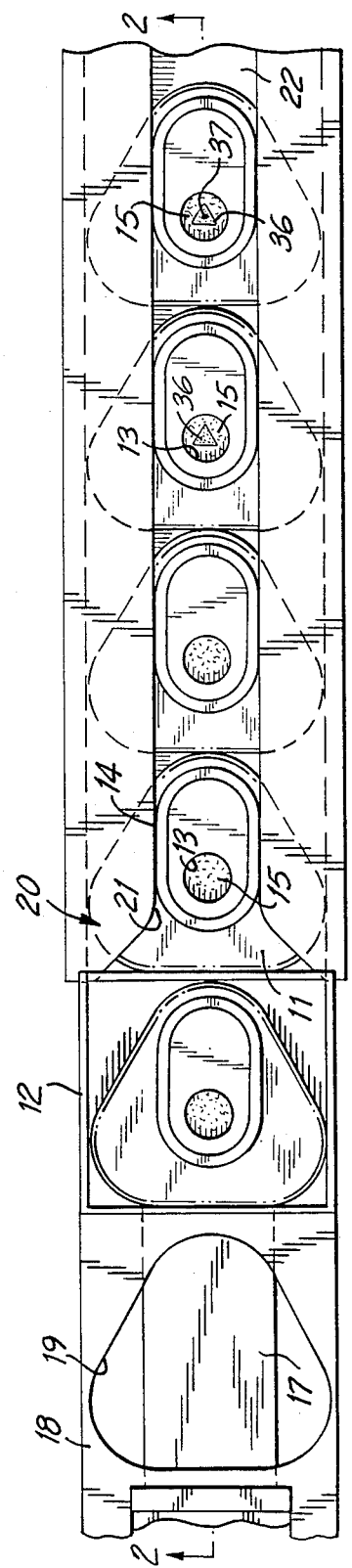
FIG. 1 shows a plan view of the system of the present invention.

Referring now to the figures, the preferred system of the present invention has a stack 10 of covers 11 loaded into a magazine 12. Each cover 11 has an aperture 13 and guide means which can conveniently be guiding wall 14. Secured to the underside of the cover is a porous support 15.

The porous support is selected to be compatible with the reagent to be coated and to have the flow characteristics desired for the diagnostic procedure to be performed with the finished device. Suitable materials for the diagnostic support include nitrocellulose, nylon, and other membranes well known to those skilled in designing diagnostic assays. The porous support can be secured to the cover by any suitable means. For example, the porous support can be secured with heat sealing, solvent welding, sonic welding or an adhesive.

A magazine 12 holds a stack of covers for delivery to a spring biased holding plate 18. The holding plate 18 has an aperture 19 therethrough. The aperture 19 is sized and dimensioned to allow the bottom-most cover 11 to pass through it when it is aligned with the cover. Below the holding plate 18 is an indexing arm 17. The clearance between the indexing arm and the holding plate is sufficient to hold only one cover.

In operation indexing arm 17 advances to push covers in a guide channel 20. At the same time holding plate 18 advances so that aperture 19 is aligned with the bottom-most cover in the magazine 12. The bottom-most cover falls through the aperture 19 and rests on indexing arm 17. When the indexing arm and holding plate have completed one stroke they retract so the cover resting on the indexing arm falls into the guide channel 20. Retraction of the holding plate takes the aperture 19 out of alignment with the covers in the magazine so that none falls through until the next stroke of the indexing arm and holding plate. The action of the indexing arm also indexes each of the covers 11 loaded in the guide channel to a next station.

The guide channel 20 has a slot 21 through its upper surface dimensioned to receive the guiding wall 14 of the cover 11. This construction assures correct orientation of the cover 11 in the guide channel 20. The guide channel is shown with a lower slot 22 running its entire length. Those skilled in the art will appreciate that the lower surface of the guide channel could be constructed as a solid table having holes through which the fluid collection heads of the coating stations can pass.

The coating stations 30 and 30A have dispensing assemblies 31 and 31A and fluid collection heads 40 and 40A. The dispensing assemblies have reservoir cannulas 32 and 32A for delivering reagents to be coated from their respective reservoirs (not shown) to dispensing cannulas 33 and 33A which are each in fluid communication with its respective reservoir cannula.

The dispensing assembly for station 30 is shown for coating in a distinct triangle pattern 36. The pattern is achieved by incorporating a template 35 into the dispensing assembly. The dispensing assembly of station 30A is shown for coating a very small dot 37 of a positive control reagent. In this case a template is not necessary.

The fluid collection head 40 has a vacuum port 41 and a frit 42. The vacuum port 41 reduces the pressure below the frit 42 sufficiently to pull a liquid through the porous support. The frit 42 is preferably dimensioned to be slightly larger than the aperture of the cover. This construction assures that suction applied through the frit pulls through the entire surface area of the porous support within the area defined by the aperture. The frit also serves to support the cover and its porous support during the coating process. When the porous support is a relatively fragile membrane (e.g. nitrocellulose) use of a frit having a surface area slightly larger than that of the aperture is particularly useful to avoid damaging the porous support during coating. This feature is particularly important to avoid performance problems with the finished diagnostic device because flow rates across the porous support are important to efficacy of the device. The fluid collection head preferably includes a compressible washer below the frit 42 to cushion the frit as it contacts the lower surface of the cover and the porous support. This cushion allows for variations within a tolerance of the thickness of the porous support.

The reciprocating means for each coating station is shown as two pneumatic cylinders 34 and 43 for coating station 30 and 34A and 43A for coating station 30A. Cylinders 34 and 34A serve to move the dispensing cannulas into and out of close proximity with the porous support. Cylinders 43 and 43A serve to move the fluid collection head into and out of contact with the lower surface of the porous support.

Preferably reciprocating cylinder 34, dispensing cannula 33 and template 35 are formed as a subassembly which is easily removable from the coating station assembly. Also preferred is construction of reciprocating cylinder 34A and dispensing cannula 33A as a single subassembly. These constructions allow rapid exchange of the subassemblies so that the ragents, pattern(s) or both to be coated can be changed when desired.

In use a cover is delivered to the guide channel as described above. The indexing arm 17 urges the cover 11 into and along the guide channel 20. Preferably one stroke of the indexing arm 17 advances each cover 11 in the guide channel 20 by one station. When the aperture 13 of a cover reaches coating station 30 cylinder 43 is extended to support the cover and its porous support as the dispensing assembly is lowered by extension of cylinder 34. Simultaneously with extension of cylinder 43, or thereafter, cylinder 34 lowers so that the template 35 contacts the porous support and the dispensing cannula 33 is in close proximity to the porous support. When the two reciprocating cylinders 34 and 43 are fully extended the fluid in the reservoir cannula 32 is allowed to flow into the dispensing cannula 33 and from there onto the porous support 15. The reduced pressure in the fluid collection head 40 pulls the fluid through the porous support leaving the reagent in the fluid secured to the porous support.

After the reagent has been coated at station 30 the cylinders 34 and 41 retract and the indexing arm 17 pushes the first cover in the guide channel which in turn causes the other covers in the guide channel to advance so that the cover just coated at station 30 is pushed to station 30A where another reagent can be coated. As can readily be appreciated, any number of coating stations can be combined in a single system. Also each dispensing assembly can incorporate any number of dispensing cannulas. Thus a single reagent can be coated from a plurality of cannulas or multiple reagents can be coated at the same station using multiple cannulas. Similarly, the template can have a single pattern or a plurality of patterns. The system of the present invention is particularly useful because it is amenable to so many variations in coating patterns by simply changing the dispensing subassembly and configuring the line with multiple coating stations in series.

What is claimed is:

1. A method of coating at least one reagent onto a porous support comprising:
   providing a cover having an upperside, an underside, and an aperture therethrough; the cover having secured to its underside an upper surface of the porous support so that the porous support covers the aperture on the underside of the cover;
   positioning the cover in a coating station with its aperture between a dispensing assembly above the cover having a dispensing cannula and a fluid collection head below the cover;
   decreasing the distance between the dispensing assembly and the fluid collection head until the fluid collection head contacts the lower surface of the porous support and the dispensing cannula is sufficiently close to the porous support that a fluid dispensed through the dispensing cannula will contact the porous support within an area defined by the aperture; and
   dispensing reagent from the dispensing cannula while reducing the pressure in the fluid collection head so that fluid in the reagent is pulled through the porous support.

2. The method of claim 1 wherein the dispensing assembly includes a template and the distance between the dispensing assembly and the fluid collection head is decreased until the template contacts the upper surface of the porous support through the aperture so that reagent dispensed from the dispensing cannula will coat the porous support in a distinct pattern defined by the template.

3. The method of claim 2 further comprising coating an additional reagent by:
   positioning the cover in a second coating station between a second dispensing assembly having a second dispensing cannula and a second fluid collection head;
   decreasing the distance between the second dispensing assembly and the second fluid collection head until the second fluid collection head contacts the lower surface of the porous support and the second dispensing cannula is sufficiently close to the porous support that a reagent dispensed through the second dispensing cannula will contact the support within the area defined by the aperture; and
   dispensing reagent from the second dispensing cannula while reducing the pressure in the fluid collection head so that fluid in the reagent is pulled through the porous support.

4. The method of claim 1 wherein the distance between the dispensing assembly and the fluid collection head is decreased by extending first and second reciprocating cylinders which are connected to the dispensing assembly and the fluid collection head respectively.

5. A system for coating at least one reagent on a porous support secured to an underside of a cover, the cover having guide means associated therewith and an aperture therethrough which is covered by the porous support comprising:

a slotted guide channel having upper and lower surfaces, the upper surface having a slot along its length which is dimensioned to receive the guide means of the cover and the lower surface having an opening therethrough;

a coating station having a dispensing assembly and a fluid collection head, the coating station being positioned with the dispensing assembly above the slot and the fluid collection head below the opening in the channel, the dispensing assembly having a dispensing cannula, and the fluid collection head having vacuum means for pulling fluid in a reagent dispensed from the dispensing cannula through a porous support positioned in the guide channel; and reciprocating means for decreasing the distance between the dispensing assembly and the fluid collection head so that a porous support and its cover positioned in the guide channel between the dispensing assembly and the fluid collection head is contacted by the fluid collection head on its lower surface and is sufficiently close to the dispensing cannula that a reagent dispensed from the dispensing cannula will contact the porous support in the area defined by the aperture in the cover.

6. The system of claim 5 wherein the reciprocating means is comprised of a first and second cylinders which are connected to the dispensing assembly and fluid collection head respectively.

7. The system of claim 6 wherein the first and second cylinders are pneumatic air cylinders.

8. The system of claim 5 wherein the dispensing assembly includes a template and the reciprocating means is for decreasing the distance between the dispensing assembly and the fluid collection head until the template contacts the porous support on its upper surface through the aperture in the cover.

9. The system of claim 6 wherein the dispensing assembly includes a template and the reciprocating means is for decreasing the distance between the dispensing assembly and the fluid collection head until the template contacts the porous support on its upper surface through the aperture in the cover.

10. The system of claim 6 wherein the second cylinder is for extending the fluid collection head through the opening in the lower surface of the guide channel so that the fluid collection assembly contacts a lower surface of a porous support, supporting the cover and porous support while the first cylinder extends to bring the dispensing cannula into close proximity with the porous support.

11. The system of claim 9 wherein the second cylinder is for extending the fluid collection head through the opening in the lower surface of the guide channel so that the fluid collection assembly contacts a lower surface of a porous support, supporting the cover and porous support while the first cylinder extends to bring the dispensing cannula into close proximity with the porous support.

12. The system of claim 5 further comprising a magazine for holding a plurality of covers and an indexing means for delivering a cover from the magazine to the guide channel and for positioning the cover in the coating station.

13. The system of claim 8 further comprising a magazine for holding a plurality of covers and an indexing means for delivering a cover from the magazine to the guide channel and for positioning the cover in the coating station.

14. The system of claim 10 further comprising a magazine for holding a plurality of covers and an indexing means for delivering a cover from the magazine to the guide channel and for positioning the cover in the coating station.

15. The system of claim 11 further comprising a second coating station.

16. The system of claim 12 further comprising a second coating station.

17. The system of claim 13 further comprising a second coating station.

18. The system of claim 6 further comprising a plurality of dispensing cannulas within the dispensing assembly.

* * * * *